(12) United States Patent
Thomas et al.

(10) Patent No.: US 12,066,214 B2
(45) Date of Patent: Aug. 20, 2024

(54) INTEGRATED ACTIVE DURATION UVC EXPOSURE FOR AIR CURTAIN

(71) Applicants: Philip Thomas, Prospect, PA (US); David Johnson, New Castle, PA (US); David Rimbey, McKees Rocks, PA (US)

(72) Inventors: Philip Thomas, Prospect, PA (US); David Johnson, New Castle, PA (US); David Rimbey, McKees Rocks, PA (US)

(*) Notice: Subject to any disclaimer, the term of this patent is extended or adjusted under 35 U.S.C. 154(b) by 415 days.

(21) Appl. No.: 17/544,086

(22) Filed: Dec. 7, 2021

(65) Prior Publication Data
US 2022/0186951 A1   Jun. 16, 2022

Related U.S. Application Data

(60) Provisional application No. 63/125,060, filed on Dec. 14, 2020.

(51) Int. Cl.
| | |
|---|---|
| *A61L 9/20* | (2006.01) |
| *F24F 8/22* | (2021.01) |
| *F24F 9/00* | (2006.01) |

(52) U.S. Cl.
CPC .............. *F24F 8/22* (2021.01); *A61L 9/20* (2013.01); *F24F 9/00* (2013.01)

(58) Field of Classification Search
CPC .............. F24F 8/22; F24F 9/00; A61L 9/20
USPC ............................. 250/455.11, 435
See application file for complete search history.

(56) References Cited

U.S. PATENT DOCUMENTS

| | | |
|---|---|---|
| 5,984,649 A | 11/1999 | Kato et al. |
| 8,568,210 B1 | 10/2013 | Thomas, Jr. et al. |
| 2005/0000509 A1* | 1/2005 | Carter .................. F24C 15/20 126/299 F |
| 2021/0402040 A1* | 12/2021 | Botts .................. A61B 90/35 |

* cited by examiner

*Primary Examiner* — Kiet T Nguyen
(74) *Attorney, Agent, or Firm* — Harpman + Harpman

(57) ABSTRACT

An air curtain air cleaner and sanitation system that incorporates established active UVC light projection technology with threshold air delivery air curtains to provide conditioned airflow by outward UVC light beam projection into the return airflow in a structure while maintaining an air control barrier between openings in a structure.

5 Claims, 4 Drawing Sheets

INTEGRATED ACTIVE DURATION UVC EXPOSURE FOR AIR CURTAIN

This application claims the benefit of U.S. Provisional Application No. 63/125,060 filed on Dec. 14, 2020.

BACKGROUND OF THE INVENTION

1. Technical Field

This invention relates to the field of air curtains used to create an airflow defined barrier in openings and structures between interior and exteriors for different conditioned spaces within a structure for environmentally retention there between and active air disinfection by prolonged exposure to UVC light.

2. Description of Prior Art

Prior art air curtains have provided air blower assemblies that include air streaming conditioning such as heating and minimal ambient air filtration and recirculation as it leaves the blower through a directional outlet nozzle to provide a laminar airflow barrier as required. Examples of such air curtains can be seen in U.S. Pat. No. 5,984,649 and applicants U.S. Pat. No. 8,568,210 which discloses venturi heating elements within an air curtainconfiguration.

Prior art air disinfection systems have been developed that rely on UVC light constructions within defined airflow passageways or UVC light directed onto air impinged surfaces for limited sanitation with the air transferring within the air transfer enclosure.

Such UVC light systems for air treatment define airflow speed within fan containment enclosures to purify air as it passes there through.

SUMMARY OF THE INVENTION

An air curtain unit with enhanced projection airflow conditioning properties having multiple blower fans with elongated air outlet directing discharge vanes and air intake directional baffles with multiple UVC light projection bulbs to produce directed outward UVC light beam into the return airstream before air curtain intake and conditioning. UVC light bulbs are known for effective air environmental sanitation based on duration of UVC exposure. Such direct UVC light radiation above the occupied area in the structure thereby provides an extended contact duration with the return air stratification induced by the air curtain's bilateral airstream after floor contact.

DETAILED DESCRIPTION OF THE INVENTION

Figure 1:
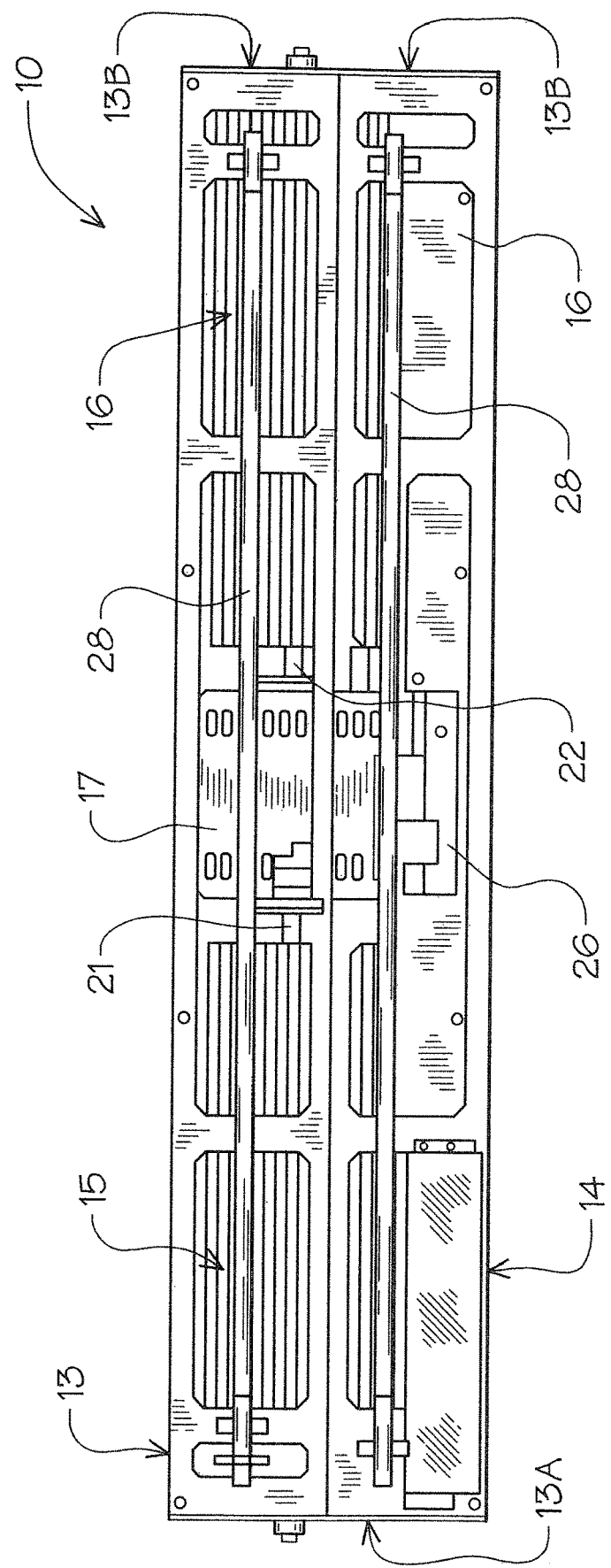
FIG. 1 is a side elevational view of the air curtain UVC beam generation system of the invention with portions cut away.
Figure 2:
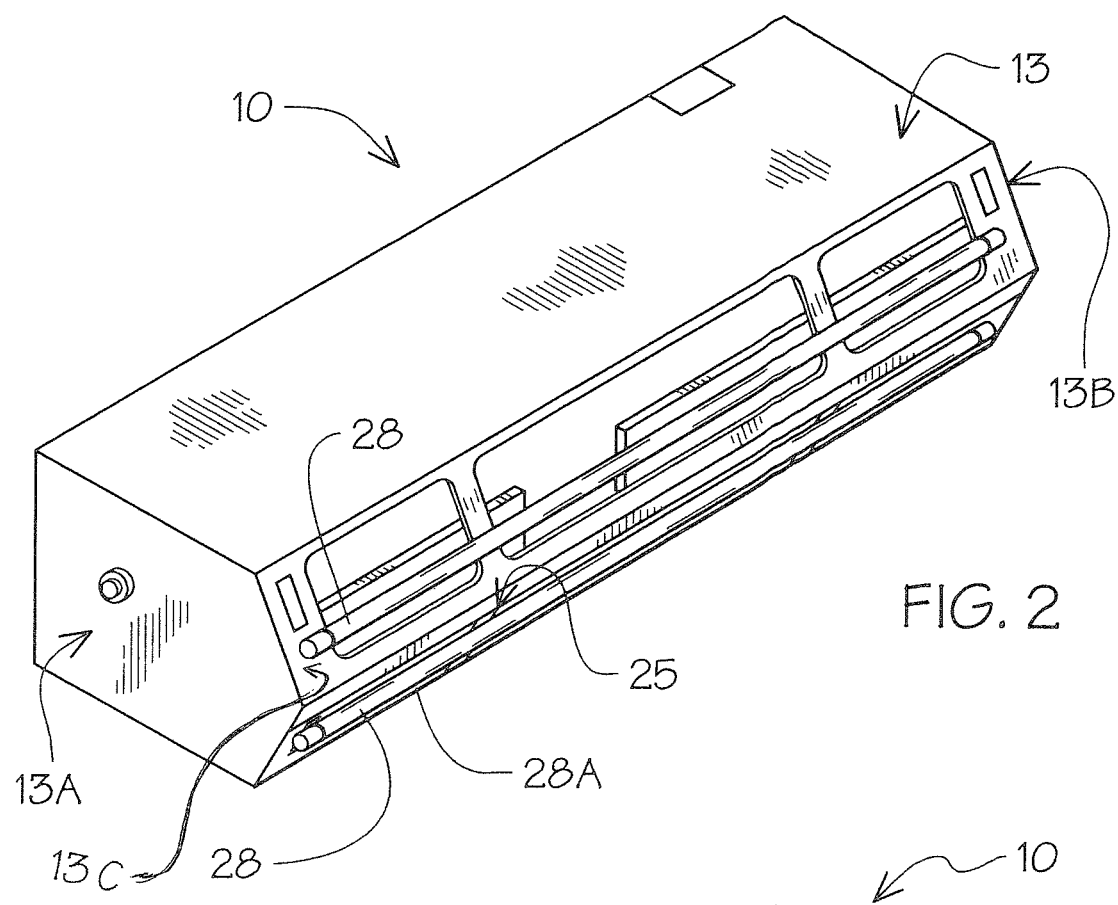
FIG. 2 is a perspective view of the air curtain with a portion removed.
Figure 3:
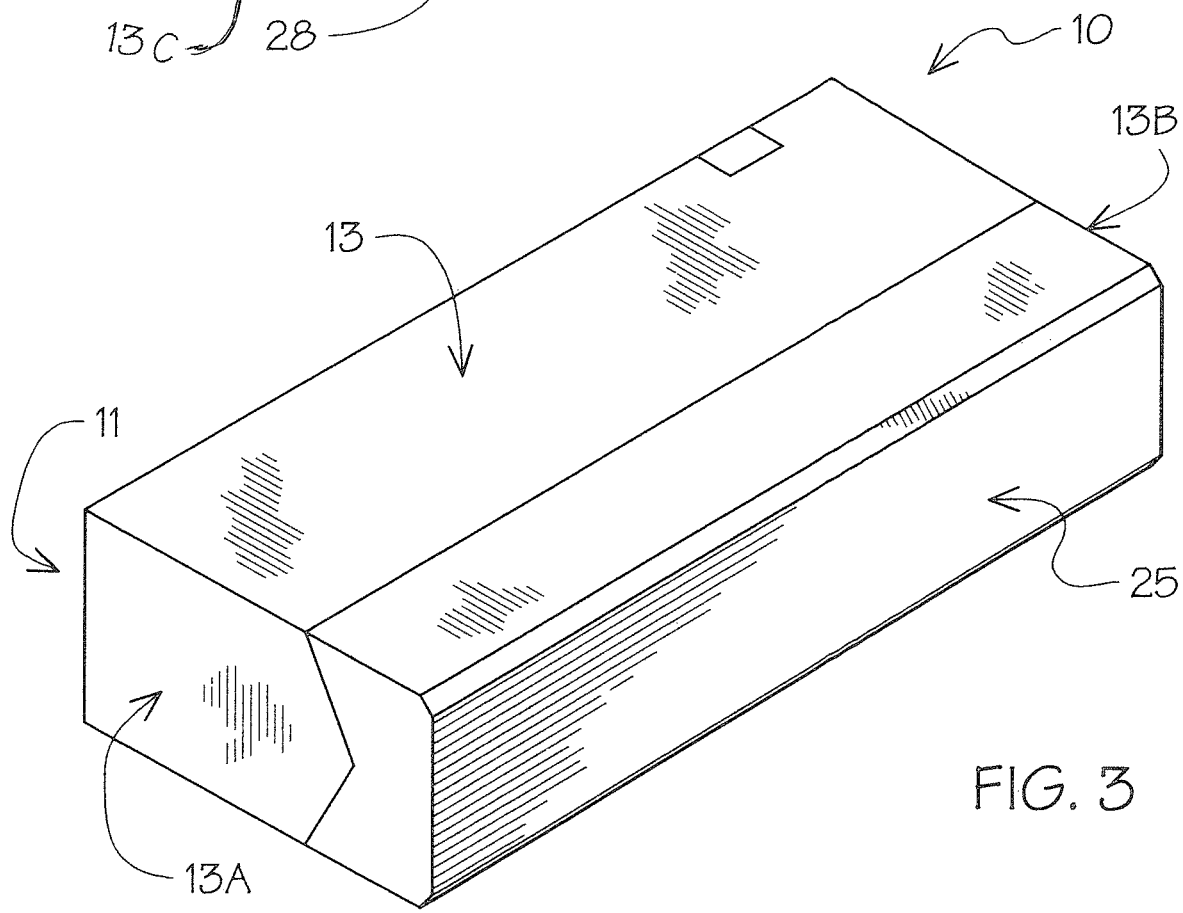
FIG. 3 is a perspective view of the assembled UVC air curtain.
Figure 4:
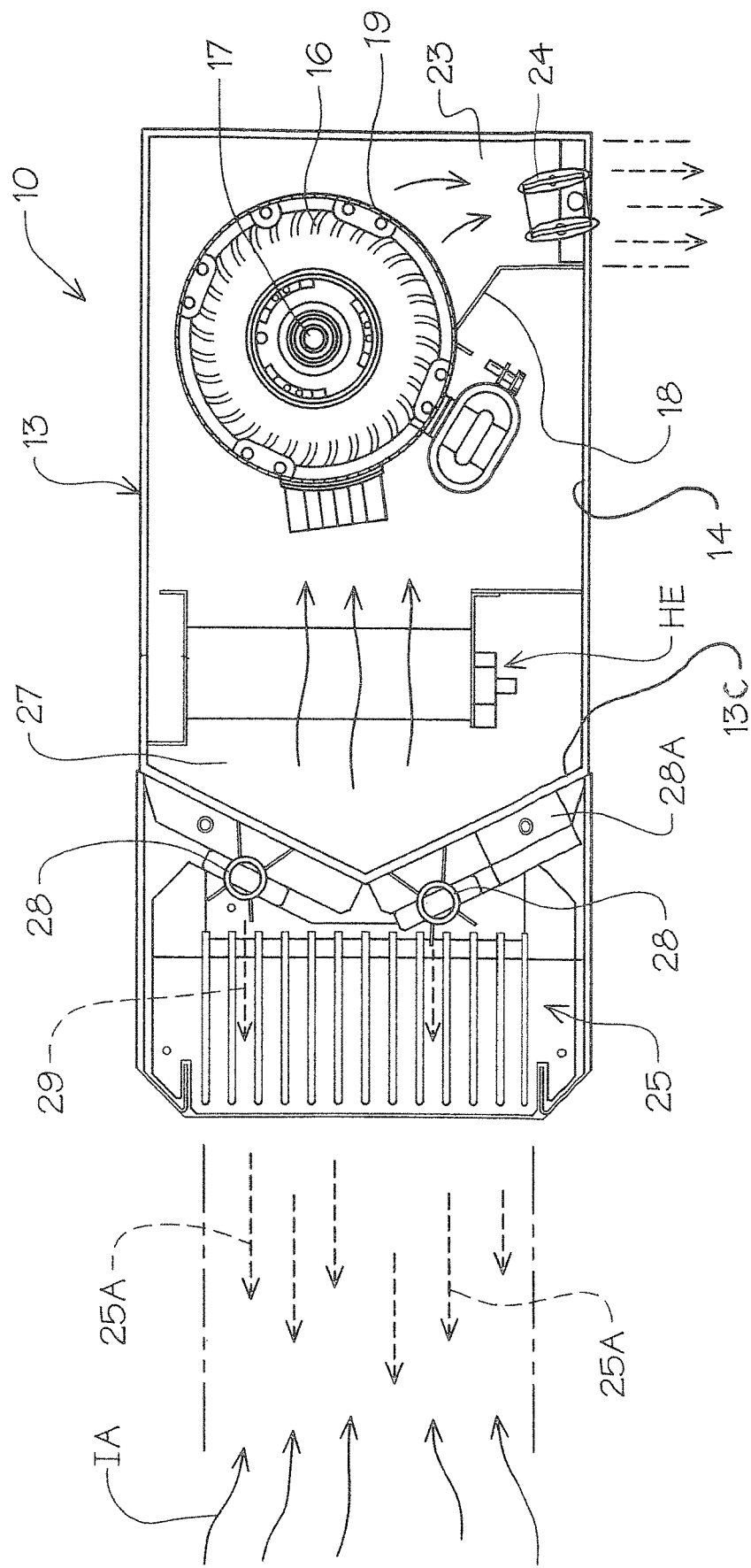
FIG. 4 is an enlarged end elevational view thereof with portions cut away illustrating return air treatment inflow and outflow.

Referring to FIGS. 1, 2 and 4 of the drawings, an enhanced UVC light air treatment air curtain assembly 10 of the invention can be seen having a generally rectangular housing 11 with wall mounting wall portion 12 and, in this example, a top 13, an end wall enclosure panels 13A and 13B and integral base pan 14 extending therefrom. A pair air blower assemblies 15 and 16 have an interconnected central drive electric motor assembly 17 mounted there between for bi-directional driving as is well known within the art. The electric motor assembly 17 is mounted within a blower assembly frame 18 extending from the surface base pan 14 of the housing 11.

The blower assembly frame 18 supports a blower housing 19 with respective blower fan cages supported in rotational relationship therein and are connected to and driven by respective motor drive shafts 21 and 22 of the electric motor assembly 17. A blower outflow chase 23 is integrally formed by the blower housing 19 with an elongated adjustable nozzle outlet 24. A unitized rectangular air inlet and light directional inlet baffle assembly 25 is removably mounted to a corresponding opening in a front wall 13C of the housing 11.

A unit power supply and control panel 26 is positioned adjacent the motor assembly 17, in this example, within the housing 11, best seen in FIG. 1 of the drawings which will provide integrated proportional programmable power and control to the air curtains components as will be well understood by those skilled in the art.

The hereinbefore described air curtain housing 11 therefore defines an interior return airflow path with recirculation inlet air IA being drawn through the return air inlet baffle assembly 25 into a downstream conditioning chamber 27 defined between the inlet baffle assembly 25 and the hereinbefore described blower assemblies 15 and 16. A heater element HE provides for conditioning air from the blower assemblies 15 and 16 indicated by inflow arrows IA.

The return inlet air flow IA is treated by one or more UVC bulbs 28 between the inlet baffle assembly 25 and the return air conditioning chamber 27, as best seen again in FIGS. 4 and 5 of the drawings, as described in greater detail hereinafter.

Figure 5:
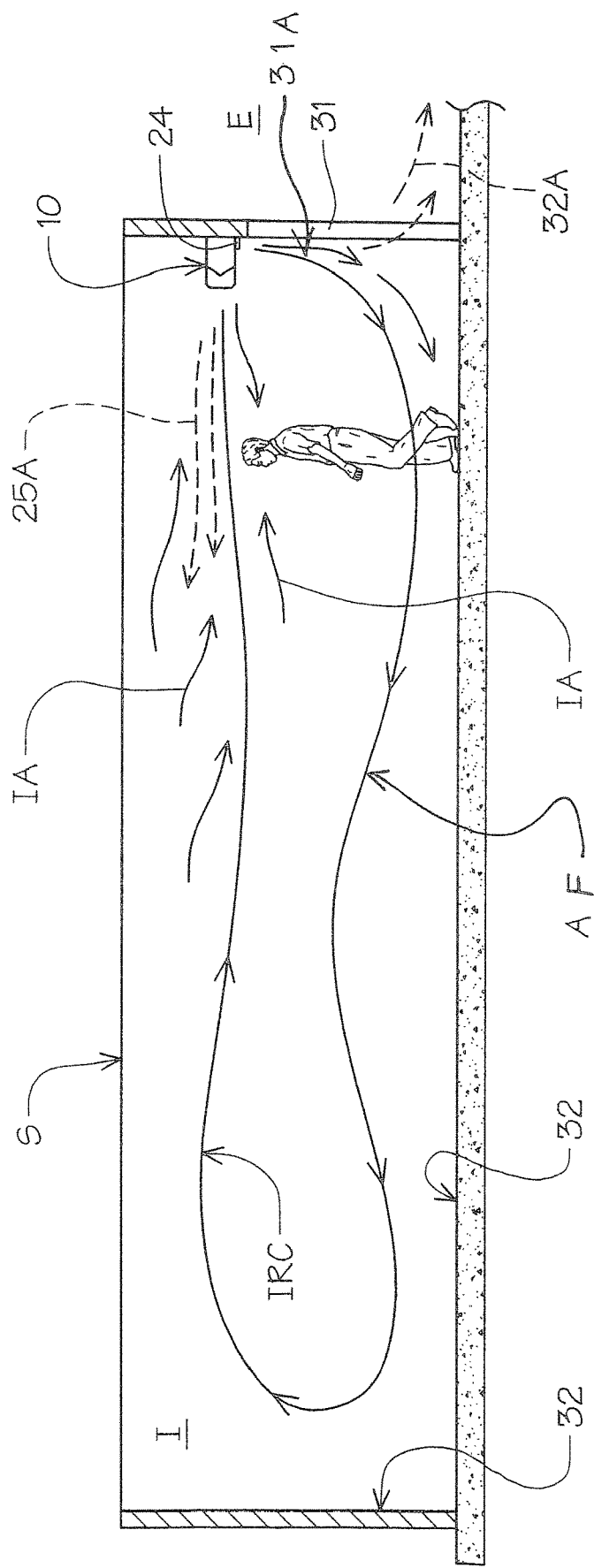
FIG. 5 is a graphic illustration of the UVC beam treatment inflow of the air curtain of the invention installed in a threshold doorway between interior and exterior environments of a structure.

The UVC bulbs 28 are powered by a UVC bulb ballast 28A via power control panel 26 and will project a beam of UVC light 29 from the unit into structure and the stratified return air laminate stream as seen best in FIGS. 4 and 5 of the drawings.

UVC light is electro-magnetic radiation with short wave lengths. UVC is termed as germicidal UV generally and is of a wave length between 200 NM and 300 NM which are strongly absorbed by nucleus acids resulting in the death or inactivation of the organism so targeted.

UVC light generated in the inlet baffle assembly 25 as a directed beams 25A provides the required UV intensity to time ratio producing a room air treatment stratification as illustrated in FIG. 5 of the drawings with UVC light flow indicated by directional arrows and corresponding structure air circulation induced by induced return incoming recirculation airflow arrows IRC towards the air curtain inflow inlet baffle assembly 25.

It will therefore be apparent that the UVC light treatment air curtain assembly 10 of the invention when mounted above the traditional threshold structure opening 31 as seen in FIG. 5 of the drawings will impart airflow paths within the structure S forming a dual stratified circulation into the structure interior I, indicated by directional airflow arrows AF as it is deflected off interior engagement surfaces 32 of the structure S. The flow velocity at 31A generated by the UVC air curtain assembly 10 will therefore push into the structure S interior I and then be returned in a recirculation pattern IRC for extended exposure to the UVC light beam directed by the air curtain inflow inlet baffle assembly 25.

The high velocity air curtain separation of interior I and exterior E achieved will be by flow vector determination providing a 30% by volume airflow from the air current flow out to the exterior indicated at 32A in FIG. 5 of the drawings. Thereby providing the bulk of the UVC beam treated airflow to circulate within the interior I of the structure as illustrated for recirculation pattern thereby.

It will thus be seen that a new and novel application of air curtain UVC projection radiation treated inflow and outflow of airflow has been illustrated and described in building threshold opening traditional air curtain applications as well as alternate nontraditional interior positional placement to treat large volume interior structures with the advantages of active UVC radiation projection duration to achieve enhanced air quality. It will be apparent to those skilled in the art that various changes and modification may be made thereto without departing from the spirit of the invention, therefore I claim:

The invention claimed is:

1. UVC light source for an air curtain comprises: an air curtain assembly having a plurality of blower units, each blower unit having an axle impellor cage driven by an electric motor and a source of power for applied voltage to said motor,
   a housing for each of said impellor cages, defining a directional nozzle airflow outlet and a return air inlet baffle assembly aligned with each of said respective impellor cages,
   a heating element within a downstream air conditioning chamber,
   said UVC light source positioned between said inlet baffle assembly and said conditioning chamber,
   said UVC light source generating a germicidal UV radiation beam directed to said return air inlet baffle assembly as UV treatment airflow paths within a structure,
   said UVC light source within said air curtain assembly mounted above a threshold opening in a structure.

2. The UVC light source for an air curtain assembly set forth in claim 1 wherein said UVC light source comprises,
   at least one UVC light bulb powered by a ballast with a source of electrical energy.

3. The UVC light source for an air curtain assembly set forth in claim 1 wherein said UV treatment airflow paths within said structure comprises,
   dual stratified air circulation by directing off of interior structure engagement surfaces beyond said threshold structure in said structure.

4. The air curtain assembly set forth in claim 3 wherein said dual stratification air circulation further comprises:
   Said air curtain assembly projecting a high velocity air curtain in said threshold opening defining a separation of structure interior and structure exterior by providing 30% by volume exterior air outflow and 70% by volume internal airflow reflecting off of interior engagement surfaces of said structure defining a return recirculation pattern of extended exposure to a said UVC light beam from said return air baffle inlet of said air curtain assembly.

5. The UVC light source for an air curtain assembly set forth in claim 1 wherein said germicidal UV radiation comprises,
   electromagnetic radiation with short wave length between 200 NM and 300 NM optimal target organism associated with germicidal radiation UV air treatment within the art.

* * * * *